(12) United States Patent
LaBaer

(10) Patent No.: US 10,351,842 B2
(45) Date of Patent: Jul. 16, 2019

(54) NUCLEIC ACID-GUIDED ORDERED PROTEIN ASSEMBLIES AND METHODS

(71) Applicant: Arizona Board of Regents on behalf of Arizona State University, Scottsdale, AZ (US)

(72) Inventor: Joshua LaBaer, Chandler, AZ (US)

(73) Assignee: Arizona Board of Regents on Behalf of Arizona State University, Scottsdale, AZ (US)

(*) Notice: Subject to any disclaimer, the term of this patent is extended or adjusted under 35 U.S.C. 154(b) by 11 days.

(21) Appl. No.: 15/310,868

(22) PCT Filed: May 14, 2015

(86) PCT No.: PCT/US2015/030728
§ 371 (c)(1),
(2) Date: Nov. 14, 2016

(87) PCT Pub. No.: WO2015/175755
PCT Pub. Date: Nov. 19, 2015

(65) Prior Publication Data
US 2017/0088830 A1     Mar. 30, 2017

Related U.S. Application Data

(60) Provisional application No. 61/993,810, filed on May 15, 2014.

(51) Int. Cl.
| | | |
|---|---|---|
| G01N 33/53 | (2006.01) |
| C12Q 1/68 | (2018.01) |
| C07H 21/02 | (2006.01) |
| C07H 21/04 | (2006.01) |
| C12N 11/06 | (2006.01) |
| C07K 19/00 | (2006.01) |
| C12N 9/96 | (2006.01) |
| C12N 15/10 | (2006.01) |

(Continued)

(52) U.S. Cl.
CPC ............ *C12N 11/06* (2013.01); *C07K 19/00* (2013.01); *C12N 9/1007* (2013.01); *C12N 9/1029* (2013.01); *C12N 9/14* (2013.01); *C12N 9/2437* (2013.01); *C12N 9/96* (2013.01); *C12N 15/10* (2013.01); *C12N 15/1068* (2013.01); *C12P 19/02* (2013.01); *C12P 19/14* (2013.01); *C12Y 201/01063* (2013.01); *C12Y 203/01* (2013.01); *C12Y 302/01004* (2013.01); *C12Y 308/01005* (2013.01)

(58) Field of Classification Search
None
See application file for complete search history.

(56) References Cited

U.S. PATENT DOCUMENTS

| | | | | |
|---|---|---|---|---|
| 8,609,344 B2 * | 12/2013 | Labaer | ............... | C07K 1/047 435/7.1 |
| 2012/0033000 A1 | 2/2012 | Darzins et al. | | |
| 2012/0033001 A1 | 12/2012 | Darzins et al. | | |

OTHER PUBLICATIONS

Diez. NAPPA as a Real New Method for Protein Microarray Generation. Microarrays (Basel). Apr. 24, 2015;4(2):214-27.*

(Continued)

*Primary Examiner* — Yong D Pak
(74) *Attorney, Agent, or Firm* — Quarles & Brady LLP

(57) ABSTRACT

Nucleic acid-guided ordered protein assembly (NOPA) arrays and methods for their generation and related applications are disclosed herein.

9 Claims, 6 Drawing Sheets

Specification includes a Sequence Listing.

(51) Int. Cl.
 *C12N 9/10* (2006.01)
 *C12N 9/14* (2006.01)
 *C12N 9/42* (2006.01)
 *C12P 19/02* (2006.01)
 *C12P 19/14* (2006.01)

(56) References Cited

OTHER PUBLICATIONS

Hinner et al., 'How to obtain labeled proteins and what to do with them' Current Opinion in Biotechnology, vol. 21, Issue 6, pp. 766-776 (2010).
Los et al., 'HaloTag: a novel protein labeling technology for cell imaging and protein analysis' ACS Chemical Biology, vol. 3, No. 6, pp. 373-382 (2008).
Mali et al., 'Barcoding cells using cell-surface programmable DNA-binding domains' Nature Methods, vol. 10, No. 5, pp. 403-406 (2013).
Lee et al., 'Emerging protein array technologies for proteomics' Expert Review of Proteomics, vol. 10, Issue 1, pp. 65-75 (2013).
International Search Report from Parent PCT No. PCT/US2015/030728, dated Jul. 24, 2015, 2 pages.
Hinner et al., 'How to obtain labeled proteins and what to do with them' Current Opinion in Biotechnology, vol. 21, 6, pp. 766-776 (2010).

\* cited by examiner

NUCLEIC ACID-GUIDED ORDERED PROTEIN ASSEMBLIES AND METHODS

CROSS-REFERENCE TO RELATED APPLICATIONS

This application is a 371 U.S. National Entry of International Application No. PCT/US2015/030728, filed May 14, 2015, which claims priority to U.S. Provisional Application No. 61/993,810 filed May 15, 2014, each of which is incorporated by reference herein for all purposes in its entirety.

BACKGROUND

Protein-protein interactions and assembly of multiprotein assemblies within cells are a core theme running throughout biology, e.g., mitochondrial multienzyme protein assemblies and multiprotein assemblies for bacterial polyketide and other secondary metabolite synthesis. However spatially controlled assembly of multiple protein actors in vitro, e.g., for the generation of artificial biosynthetic pathways, remains a daunting challenge. In particular, there is an ongoing need for methods and compositions that allow controlled spatial localization of proteins ex vivo on artificial substrates, e.g., in protein arrays or 3D scaffolds.

BRIEF SUMMARY

Described herein are nucleic acid-anchored ordered protein assemblies and methods relating to their generation and application.

Accordingly, in one aspect provided herein is a method for generating a nucleic acid-anchored ordered protein assembly (NOPA), comprising: (i) providing a nucleic acid-guided protein localization (NPL) array comprising a plurality of single stranded protein localization oligonucleotides (PLOs) linked at a plurality of positions to a solid support substrate surface, wherein the plurality of PLOs comprise at least a first position-linked PLO comprising a first protein localization (PL) sequence and a second position-linked PLO comprising a second PL sequence; (ii) contacting the nucleic acid array with at least a first nucleic acid anchor (NAA) protein and a second NAA protein, wherein the first NAA is linked to an anchoring oligonucleotide comprising an anchoring sequence complementary to the first PL sequence, and the second NAA protein is linked to an anchoring oligonucleotide (AO) comprising an anchoring sequence complementary to the second PL sequence; and (iii) hybridizing, under protein compatible conditions, the AOs of the first and second NAA proteins with the first and second PLOs, whereby the at least first and second NAA proteins are localized to the first and second locations to form an ordered protein assembly.

In some embodiments of the method the NAA proteins are fusion polypeptides comprising the amino acid sequence of a haloalkane dehalogenase or O6-alkylguanine-DNA alkyltransferase fused at the N-terminus or C-terminus of the fusion polypeptides. In some embodiments the NAA proteins are fusion polypeptides comprising the amino acid sequence of a haloalkane dehalogenase, each anchoring oligonucleotide comprises a 5' or 3' halotag ligand, and the haloalkane dehalogenase is covalently linked to the halotag ligand.

In some embodiments the first and second PLOs are located between 20 nm and 200 µm of each other.

In some embodiments the plurality of PLOs comprises at least four different PL sequences. In other embodiments the plurality of PLOs comprises at least ten different PL sequences.

In some embodiments the NPL array is a two dimensional array. In other embodiments the NPL array is a three dimensional array.

In another aspect provided herein is a nucleic acid-linked ordered protein assembly (NOPA), comprising (i) at least first and second single stranded protein localization oligonucleotides (PLOs) linked to a solid support substrate surface at separate positions, wherein each PLO comprises a protein localization (PL) sequence; and (ii) a first nucleic acid anchor (NAA) protein and a second NAA protein, wherein the first NAA is linked to an anchoring oligonucleotide (AO) comprising an anchoring sequence complementary to the first PL sequence, and the second NAA is linked to an anchoring oligonucleotide (AO) comprising an anchoring sequence complementary to the second PL sequence; and wherein the first and second NAA proteins are bound to the first and second PL sequences by nucleic acid duplexes between the PL sequences and the anchoring sequences. In some embodiments the NAA protein is a fusion polypeptide comprising the amino acid sequence of a haloalkane dehalogenase, each anchoring oligonucleotide comprises a 5' or 3' halotag ligand, and the haloalkane dehalogenase is covalently linked to the halotag ligand.

In some embodiments the separate positions are located between 20 nm and 200 µm of each other. In some embodiments the at least first and second PLOs are in a two dimensional array. In other embodiments the at least first and second PLOs are in a three dimensional array.

In some embodiments the NOPA comprises NAA proteins comprising at least ten different amino acid sequences. In some embodiments the NOPA comprises an enzyme selected from the group consisting of polyketide synthases, fungal cellulases, kinases, nitrogenases, proteases, phosphatases, oxidases, reductases, polymerases, hydrolases, lyases, transferases, isomerases, ligases, carboxylic acid reductases, oxidoreductases, glucosidases, glycoside hydrolases, glycases, dehydrogenases, enolases, synthases, endonucleases, exonucleases, lipases, oxygenases, cellulases, cyclases, esterases, and any combination thereof.

In a further aspect provided herein is a method for in vitro biocatalysis, comprising: (i) providing a NOPA comprising first, second, and third nucleic acid anchor (NAA) enzymes, the NAA enzymes being linked to a solid support substrate surface by a hybrid duplex formed between anchoring oligonucleotides and protein localization oligonucleotides; (ii) contacting the NOPA with a reaction mix comprising a first substrate for the first NAA enzyme, whereby the first NAA enzyme converts the first substrate to a second substrate for the second NAA enzyme, the second NAA enzyme converts the second substrate to a third substrate for the third NAA enzyme, and the third NAA enzyme converts the third substrate to an end product, wherein each NAA enzyme is covalently linked to an anchoring oligonucleotide comprising an anchoring sequence; the protein localization oligonucleotide comprises a protein localization sequence complementary to the anchoring sequence, and the protein localization oligonucleotide is covalently linked to the solid support substrate surface.

In some embodiments of the method the NAA enzymes are fusion polypeptides comprising the amino acid sequence of a haloalkane dehalogenase or O6-alkylguanine-DNA alkyltransferase fused at the N-terminus or C-terminus of the fusion polypeptides. In some embodiments each NAA enzyme is a fusion polypeptide comprising the amino acid sequence of a haloalkane dehalogenase, each anchoring oligonucleotide comprises a 5' or 3' halotag ligand, and the haloalkane dehalogenase is covalently linked to the halotag ligand.

In some embodiments the separate positions are located between 20 nm and 200 µm of each other.

In some embodiments the method further comprises the steps of (iii) releasing the first, second, and third NAA enzymes into solution by denaturing the hybrid duplex; and (iv) washing away the released enzymes to obtain a protein localization array comprising the solid support substrate surface and the protein localization oligonucleotides linked thereto.

In some embodiments the NAA enzymes are selected from the group consisting of polyketide synthases, fungal cellulases, kinases, nitrogenases, proteases, phosphatases, oxidases, reductases, polymerases, hydrolases, lyases, transferases, isomerases, ligases, carboxylic acid reductases, oxidoreductases, glucosidases, glycoside hydrolases, glycases, dehydrogenases, enolases, synthases, endonucleases, exonucleases, lipases, oxygenases, cellulases, cyclases, esterases, and any combination thereof. In some embodiments at least one of the NAA enzymes comprises the amino acid sequence of a polyketide synthase. In other embodiments at least one of the NAA enzymes comprises the amino acid sequence of a cellulase.

INCORPORATION BY REFERENCE

All publications, patents, and patent applications mentioned in this specification are herein incorporated by reference to the same extent as if each individual publication, patent, and patent application was specifically and individually indicated to be incorporated by reference.

BRIEF DESCRIPTION OF THE DRAWINGS

The present invention will be better understood and features, aspects and advantages other than those set forth above will become apparent when consideration is given to the following detailed description thereof. Such detailed description makes reference to the following drawings, wherein.

DETAILED DESCRIPTION

Figure 1:
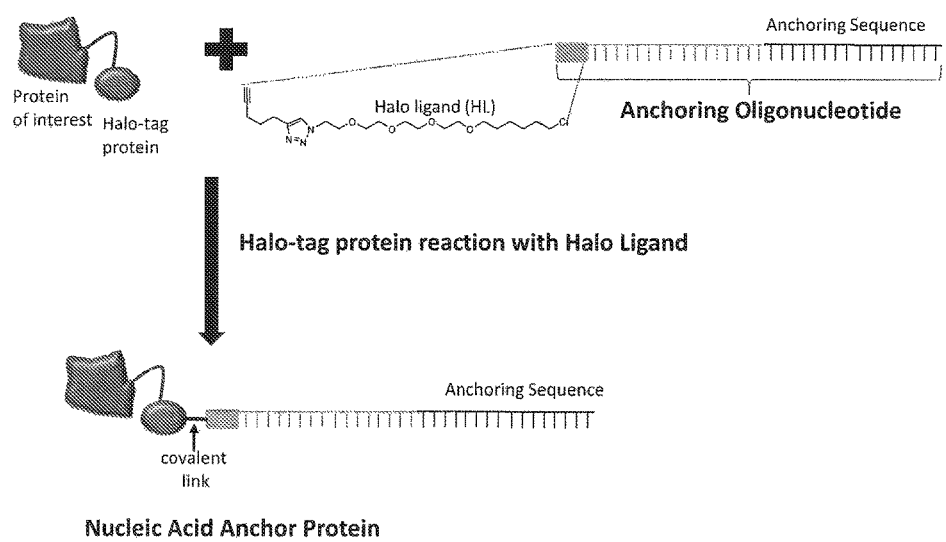
FIG. 1. Generation of a Nucleic Acid Anchor (NAA) Protein. In this non-limiting embodiment, a fusion protein includes a protein of interest fused to terminal HaloTag® protein (haloalkane dehalogenase). The fusion polypeptide is then reacted with an anchoring oligonucleotide modified at one end with a Halo ligand. The HaloTag protein reacts with the Halo ligand to form a covalent bond thereby generating the NAA protein.

In General. Before the present materials and methods are described, it is understood that this invention is not limited to the particular methodology, protocols, materials, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications and patents specifically mentioned herein are incorporated by reference for all purposes including describing and disclosing the chemicals, cell lines, vectors, animals, instruments, statistical analysis and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

The Invention. The present invention provides nucleic acid-linked ordered protein assemblies and methods for their generation and methods for their use, e.g., in in vitro biocatalytic pathways.

The compositions and methods described herein allow the assembly of specific proteins on a surface at specific positions or in a particular order (as in a protein microarray) or to attach proteins to a three dimensional scaffold (as in nanostructures). For example, in a protein array it may be useful to test a series of proteins against a particular ligand. In other applications, proteins (e.g., enzymes) arranged in a particular order would allow the proteins to be linked in series, as in a biochemical pathway. Their proximity thereby lowers energy barriers and leads to more rapid biochemical reactions. The disclosed methods are advantageous relative to known protein "printing" methods in the art, as it may be difficult to print the proteins in tight proximity to one another, particularly where very close spacing of different protein addresses (e.g., as in a nanostructure) is desired.

Unless defined otherwise, all technical and scientific terms used herein have the same meaning as commonly understood by one of ordinary skill in the art to which the invention pertains. Although any methods and materials similar to or equivalent to those described herein can be used in the practice or testing of the present invention, the preferred methods and materials are described herein.

Definitions

In describing the embodiments and claiming the invention, the following terminology will be used in accordance with the definitions set out below.

As used herein, "about" means within 5% of a stated range within the relevant parameter.

As used herein, "hybridizing under protein-compatible conditions" refers generally to conditions under which hybridization of an "anchoring sequence" to a "protein localization" sequence occurs at a temperature of about 37° C. and a total salt between about 0.5 M to about 0.6 M and a pH of about 7.0 to about 7.5. Such conditions allow specific nucleic acid hybridization to occur under conditions that substantially preserve the structure and function of NAA proteins as disclosed herein. In an exemplary embodiment, the protein-compatible hybridization conditions are 37° C., pH 7.0, and the following buffer composition: $Na_2HPO/NaH_2PO_4$ 0.1 M, NaCl 0.5 M, Tween 20 (0.65%), PEG 4000 (2%). Alternatively, protein-compatible hybridization conditions are 37° C., pH 7.5, in the following buffer: Hepes (160 mM), LiCl (0.5 M), Tween 20 (0.05%). Alternatively, the hybridization conditions described in Wacker et al (2004), *Chembiochem,* 5(4):453-459; or Wacker et al (2004), *Analytical Biochem.* 330(2):281-287.

As used herein, "nucleic acid anchor protein or enzyme" or "NAA protein or enzyme" refers to a protein that is covalently linked to a single stranded nucleic acid (nucleic acid bar code) that comprises at least an anchoring sequence that allows localization of the linked protein to a particular position within an NPL array via hybridization with a PL sequence as described herein.

As used herein, "nucleic acid-linked ordered protein assemblies," or "NOPAs" refer to sets of proteins that are tethered to a surface via nucleic acid duplexes, e.g., double stranded DNA or double stranded RNA duplexes.

As used herein, a "nucleic acid-guided protein localization (NPL) array," or "NPL array" refers to a two or three dimensional array of single stranded nucleic acids (about 18 to 70 nucleotides in length) covalently linked at their 5' or 3' end to a solid support substrate surface, e.g., derivatized glass, or a derivatized gold surface, or alternatively, hybridized to scaffolding oligonucleotides that are covalently linked to the solid support substrate surface. The single stranded nucleic acids in the NPL array comprise a nucleic acid localization (NAL) sequence.

As used herein, "oligonucleotide," refers to a polynucleotide of any length unless otherwise specified.

As used herein, a "protein localization" or "PL" sequence is a nucleic acid sequence that is linked to a position with an array and is complementary to an "anchoring sequence" and which, via hybridization with the anchoring sequence, localizes a protein linked to a nucleic acid "bar code" containing the anchoring sequence.

As used herein, "prey polypeptide target," refers to a polypeptide for which one or more bait polypeptides (e.g., an antibody) have specific affinity. The amino acid sequence of a prey polypeptide target can range from at least 5 amino acids to about 2000 amino acids.

As used herein, "population of PPTs" or "PPT library" refers to a heterogeneous mixture of polypeptides containing diverse amino acid sequences.

With respect to the amino acid sequence homology of polypeptides described herein, one of ordinary skill in the art will appreciate that structural and functional homology of two or polypeptides generally includes determining the percent identity of their amino acid sequences to each other. Sequence identity between two or more amino acid sequences is determined by conventional methods. See, for example, Altschul et al., (1997), Nucleic Acids Research, 25(17):3389-3402; and Henikoff and Henikoff (1982), Proc. Natl. Acad. Sci. USA, 89:10915 (1992). Briefly, two amino acid sequences are aligned to optimize the alignment scores using a gap opening penalty of 10, a gap extension penalty of 1, and the "BLOSUM62" scoring matrix of Henikoff and Henikoff (ibid.). The percent identity is then calculated as: ([Total number of identical matches]/[length of the longer sequence plus the number of gaps introduced into the longer sequence in order to align the two sequences])(100).

Compositions

Described herein are nucleic acid-anchored ordered protein assembly compositions, which include: (i) at least first and second protein localization oligonucleotides (PLOs) comprising chemically linked to a solid support substrate surface at separate positions on the substrate, wherein each PLO comprises a protein localization (PL) sequence; and (ii) a first nucleic acid anchor (NAA) protein and a second NAA protein, wherein the first NAA is linked to an anchoring oligonucleotide (AO) comprising an anchoring sequence complementary to the first PL sequence, and the second NAA is linked to an anchoring oligonucleotide (AO) comprising an anchoring sequence complementary to the second PL sequence; and wherein the first and second NAAs are bound to the first and second PL sequences by nucleic acid duplexes between the PLOs and the AOs.

Suitable solid support substrates include, but are not limited to, derivatized glass, derivatized metal, and derivatized carbon surfaces. NOPA solid support formats include: chips and beads.

In preferred embodiments, PLOs and AOs are single stranded DNA oligonucleotides. In other embodiments, PLOs or AOs are single stranded RNA (or modified RNA) oligonucleotides.

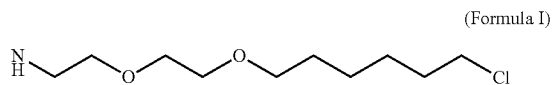 [SMILES: NCCOCCOCCCCCCCl]
(Formula I)

DNA-conjugated HaloTag® ligands can be generated by conjugating an anchoring oligonucleotide sequence with a HaloTag® ligand "building" block comprising a suitable reactive group, which reacts with the DNA to form a covalent linkage thereby generating an anchoring oligonucleotide. Suitable examples of such HaloTag® ligand building blocks include:

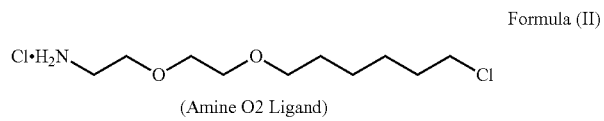
Formula (II)
(Amine O2 Ligand)

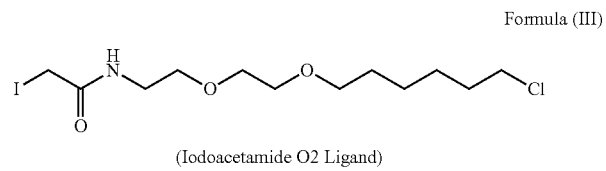
Formula (III)
(Iodoacetamide O2 Ligand)

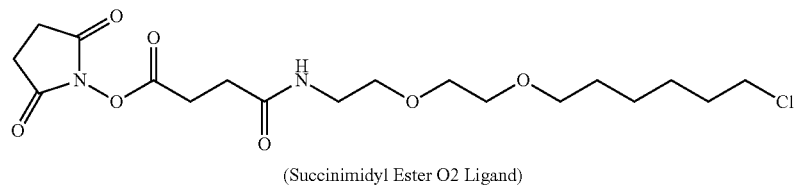
Formula (IV)
(Succinimidyl Ester O2 Ligand)

Figure 2:
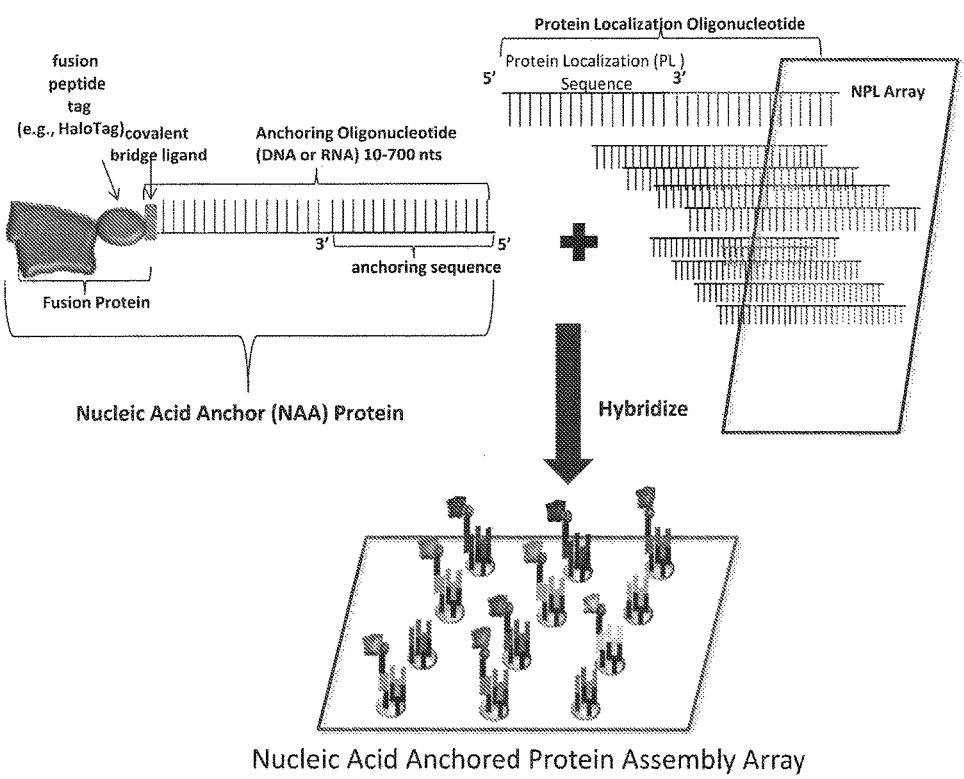
FIG. 2. Schematic Overview of Generation of a Nucleic Acid Guided Ordered Protein Assembly (NOPA) Array. A non-limiting embodiment is schematically illustrated in which NAA proteins comprising an anchoring oligonucleotide (AO) is hybridized to a nucleic acid-guided protein localization (NPL) array, comprising substrate-linked protein localization oligonucleotides (PLOs) complementary to the anchoring oligonucleotides. Hybridization of the anchoring oligonucleotides with the protein localization oligonucleotides localizes the NAA proteins to the desired positions on the array thereby forming the NOPA array.

In some embodiments, AOs and PLOs are 10 to 70 bases in length, e.g., about 12, 14, 18, 20, 22, 25, 30, 32, 35, 40, 45, 50, 60, 65, or another number of bases in length from about 10 to about 70 bases. In some embodiments, an anchoring sequence or a protein localization sequence are about 10-40 nucleotides in length. One embodiment of this nucleic acid anchoring (aka "bar coding") configuration is illustrated in FIGS. 1-2.

In some embodiments, NAA proteins are fusion polypeptides, which comprise the amino acid sequence of a haloalkane dehalogenase tag ("HaloTag®"; SEQ ID NO 1) polypeptide fused at their N-terminus or C-terminus.

(HaloTag ® Amino Acid Sequence)
SEQ ID NO: 1
MAEIGTGFPFDPHYVEVLGERMHYVDVGPRDGTPVLFLHGNPTSSYVWRN

IIPHVAPTHRCIAPDLIGMGKSDKPDLGYFFDDHVRFMDAFIEALGLEEV

VLVIHDWGSALGFHWAKRNPERVKGIAFMEFIRPIPTWDEWPEFARETFQ

AFRTTDVGRKLIIDQNVFIEGTLPMGVVRPLTEVEMDHYREPFLNPVDRE

PLWRFPNELPIAGEPANIVALVEEYMDWLHQSPVPKLLFWGTPGVLIPPA

EAARLAKSLPNCKAVDIGPGLNLLQEDNPDLIGSEIARWLSTLEISG

Where the NAA proteins are fusion polypeptides comprising a HaloTag® amino acid sequence, anchoring oligonucleotides comprise a HaloTag® ligand comprising the structure of Formula I shown below, which enables efficient and convenient chemical linkage of the anchoring oligonucleotide to a fusion polypeptide via reaction of the ligand with the fused HaloTag® amino acid sequence:

HaloTag® polypeptide expression vectors and building block ligands are available commercially from Promega (Madison, Wis.) and are conjugated with nucleic acids according to the manufacturer's instructions. In some embodiments, to conjugate a HaloTag® ligand to a DNA sequence, the DNA sequence is modified with an alkyne group (Integrated DNA technology). The azido halo ligand is then reacted with the alkyne terminated DNA sequence using the Cu-catalyzed cycloaddition ("click" chemistry). See, e.g., Duckworth et al (2007), *Angew Chem. Int.,* 46, Issue 46, pages 8819-8822.

Alternatively, other fusion peptide tag-ligand anchoring oligonucleotide systems can be used, e.g., O6-alkylguanine-DNA alkyltransferase, reacts specifically and rapidly with benzylguanine (BG) (known as the SNAP-tag system from New England Biolabs) or the "CLIP-tag®" variant of this system, also from New England Biolabs). See also Keppler et al (2003), *Nat Biotechnol*, (1):86-99; and Gautier et al (2008), *Chem. Biol,* 15(2):128-136.

In some embodiments, a NOPA comprises a plurality of polypeptides comprising a plurality of amino acid sequences derived from enzymes including, but not limited to. polyketide synthases, fungal cellulases, kinases, nitrogenases, proteases, phosphatases, oxidases, reductases, polymerases, hydrolases, lyases, transferases, isomerases, ligases, carboxylic acid reductases, oxidoreductases, glucosidases, glycoside hydrolases, glycases, dehydrogenases, enolases, synthases, endonucleases, exonucleases, lipases, oxygenases, cellulases, cyclases, esterases, and any combination thereof.

In some embodiments, the number of different NAA protein amino acid sequences is about 5 to about 100. In further embodiments, the number of amino acid sequences is about 100 to about 1,000.

In some embodiments the positions of protein localization oligonucleotides on a solid support substrate surface are located about 20 nm to about 200 µm, e.g., about 50 nm, 100 nm, 200 nm, 500 nm, 1 µm, 2 µm, 5 µm, 10 µm, 50 µm, 100 µm, 150 µm or another spacing distance from about 20 nm to 200 µm.

In some embodiments a NOPA comprises at least ten different NAA proteins, each NAA protein comprising a distinct amino acid sequence. In some embodiments, the NOPA comprises at least three to about 50 NAA proteins, e.g., 4, 6, 8, 10, 12, 15, 20, 30, 35, 40 or another number of NAA proteins from at least three to about 50 NAA proteins.

Figure 4:
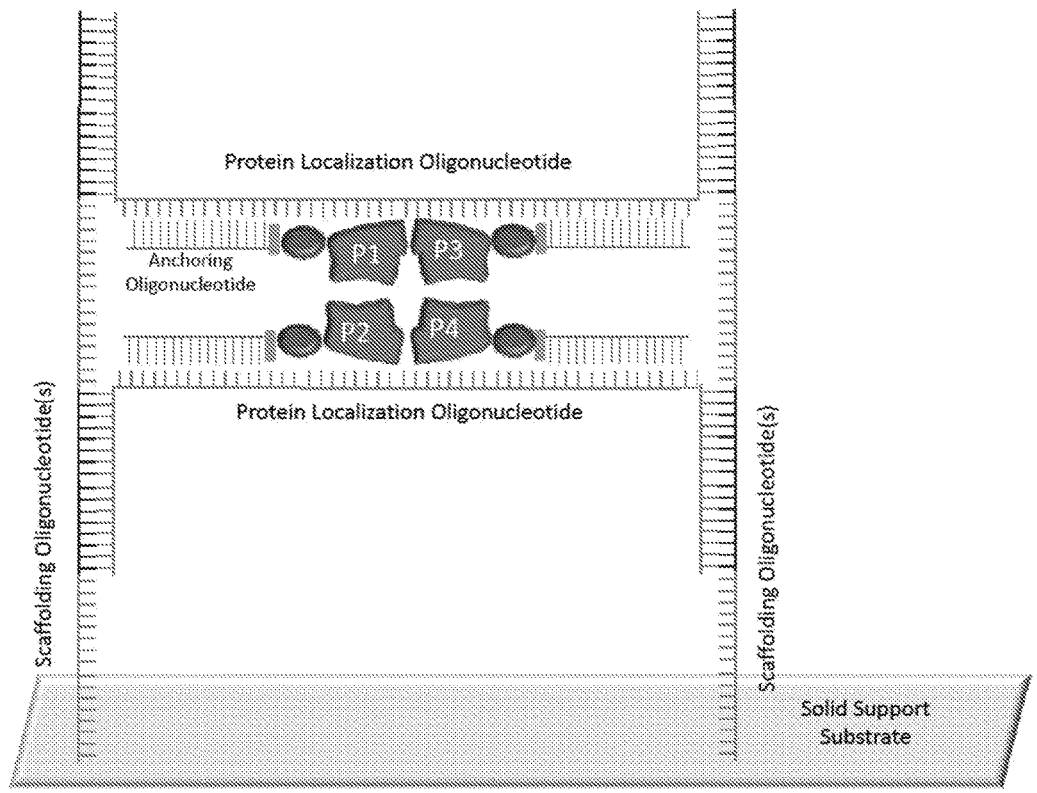
FIG. 4. Schematic illustration of a Three Dimensional Array Using DNA Scaffolding. A non-limiting embodiment is schematically illustrated in which DNA scaffolding oligonucleotides are bound to a solid support substrate surface. Multiple protein localization oligonucleotides form duplexes at multiple positions along the scaffolding oligonucleotides thereby setting the spacing of the protein localization oligonucleotides. In turn, NAA proteins (shown as P1-P4) are localized at specific positions based on the hybridization of their specific anchoring oligonucleotides with the corresponding complementary protein localization oligonucleotide. Note that in this illustration a single protein localization oligonucleotide contains multiple protein localization sequences, i.e., multiple anchoring oligonucleotides can hybridize on one protein localization oligonucleotide.
Figure 5:
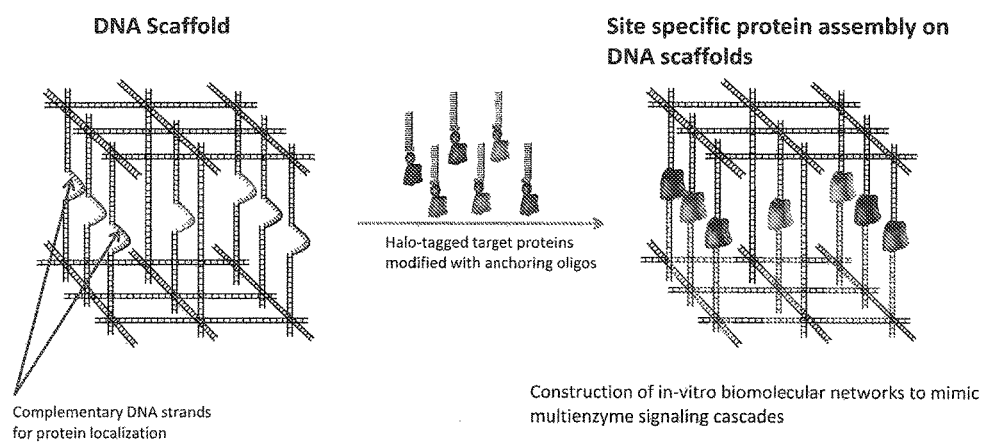
FIG. 5. Schematic overview of a three dimensional NAA-enzyme array for biocatalysis. In a non-limiting embodiment, a DNA scaffold bearing protein localization sequences is allowed to hybridize with added nucleic acid anchor (NAA) proteins (e.g., enzymes) resulting in site specific assembly of the NAA enzymes on the three dimensional scaffold to generate a an assembly of enzymes useful for in vitro catalysis.

In some embodiments, the PLOs are in a two dimensional array, e.g., a flat array on a glass slide, e.g., as illustrated schematically in FIG. 2. In other embodiments, the PLOs are in a three dimensional array, e.g., in a DNA scaffold/lattice, multilayer stacks, or dendrimers. For example, in some embodiments, a three dimensional DNA scaffolding array is formed by covalently linking scaffolding oligonucleotides to a solid support substrate surface. As illustrated in FIGS. 4-5. the scaffolding oligonucleotides comprise sequences complementary to sequences found in various protein localization oligonucleotides (PLOs), thereby permitting localization of the PLOs at various points along the scaffolding oligonucleotides by hybridization. Subsequently, NAA proteins are added to the nucleic acid scaffold and the anchoring oligonucleotides in the NAA proteins are allowed to hybridize to their respective PLOs, thereby assembling the various NAAs in a desired three dimensional configuration. In some embodiments, the nucleic acid scaffolding oligonucleotides are DNA oligonucleotides. In other embodiments the nucleic acid scaffolding oligonucleotides are RNA oligonucleotides. In some embodiments, the nucleic acid scaffolding comprises both DNA and RNA oligonucleotides. Typically, scaffolding oligonucleotides will be longer than PLOs, ranging in length from about 50 nucleotides to 150 nucleotides. The longer length of the PLOs allows them to hybridize to multiple PLOs with a desired spacing between scaffolding oligonucleotides-PLO duplexes.

Also provided herein are kits that include: (i) an NPL array; and (ii) at least two NAA proteins comprising different amino acid and anchoring oligonucleotide sequences.

Methods

Also provided herein is a method for generating a nucleic acid-anchored ordered protein assembly comprising the steps of: (i) providing a nucleic acid-guided protein localization (NPL) array comprising a plurality of single stranded protein localization oligonucleotides (PLOs) linked at a plurality of positions to a solid support substrate surface, wherein the plurality of PLOs comprise at least a first position-linked PLO comprising a first protein localization (PL) sequence and a second position-linked PLO comprising a second PL sequence; (ii) contacting the nucleic acid array with at least a first nucleic acid bar coded (NAA) protein and a second NAA protein, wherein the first NAA is linked to a nucleic acid comprising an anchoring sequence complementary to the first PL sequence, and the second NAA protein is linked to an anchoring oligonucleotide (AO) comprising an anchoring sequence complementary to the second PL sequence, and (iii) hybridizing, under protein compatible conditions, the AOs of the first and second NAA proteins with the first and second PLOs, whereby the at least first and second NAA proteins are localized to the first and second locations to form an ordered protein assembly. NPL arrays used in this method can be generated by any of a number of established methods used to generate hybridization arrays, especially DNA hybridization arrays. See, e.g., U.S. Pat. Nos. 5,445,934, 5,510,270 for generation of short oligonucleotide arrays; U.S. Pat. No. 7,041,445 for long oligonucleotide arrays; and U.S. Pat. Nos. 5,807,522 and 6,110,426 for long DNA probes, i.e., DNA probes equal to or greater than 150 nucleotides in length, e.g., 150 nucleotides to about 5,000 nucleotides, e.g., 200 nucleotides, 250 nucleotides, 500 nucleotides, 800 nucleotides, 1,000, nucleotides, 1,500 nucleotides, 2000 nucleotides, 3,000 nucleotides, 4,000 nucleotides, or another probe length from about 150 nucleotides to about 5,000 nucleotides in length.

Figure 3:
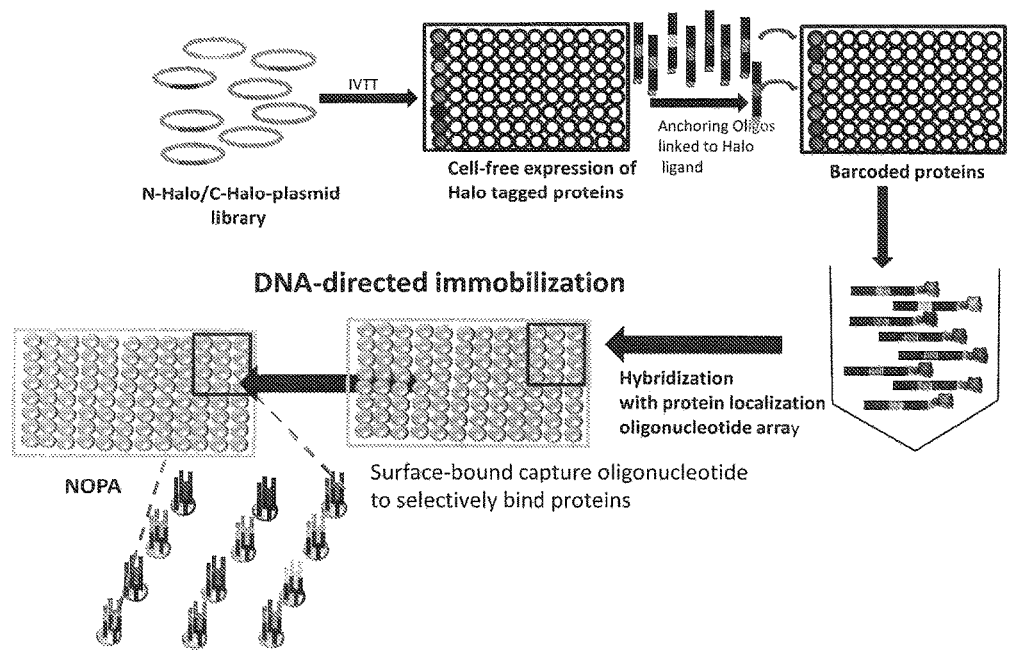
FIG. 3. Schematic overview of NOPA array generation starting from a cDNA library. A schematic illustration of a non-limiting embodiment shows a library of cDNAs encoding HaloTag® fusion proteins. These are then transcribed an in vitro translated (IVTT) in an arrayed, multiwell format. Each translated fusion protein is then individually then reacted with a specific halo ligand-linked anchoring oligonucleotide, where each anchoring oligonucleotide contains a different anchoring sequence. The resulting NAA proteins are then added to a surface-bound array of protein localization oligonucleotides complementary to the anchoring oligonucleotides. Hybridization of the anchoring oligonucleotides with the protein localization oligonucleotides results in formation of the nucleic acid-linked ordered protein assemblies (NOPAs).

Proteins for use in the disclosed methods can be generated in by any of a number methods known in the art including, but not limited to, nucleic acids programmable protein array (NAPPA), isolated capture or cover capture, protein in situ array (PISA), and DNA array to protein array (DAPA), especially when provided in a nanowell array format. Alternatively, recombinant proteins can be generated by purification from heterologous expression hosts, by any of a number of methods and systems that are well established in the art and/or commercially available. See, e.g., a schematic, non-limiting, overview in FIG. 3.

In some embodiments the NAA proteins used in this method are fusion polypeptides comprising the amino acid sequence of a haloalkane dehalogenase or O6-alkylguanine-DNA alkyltransferase fused at the N-terminus or C-terminus of the fusion polypeptides. In some embodiments the NAA proteins are fusion polypeptides comprising the amino acid sequence of a haloalkane dehalogenase, and wherein the NAA proteins are linked to the nucleic acids comprising the anchoring sequences via a covalent bond between the haloalkane dehalogenase and a halotag ligand.

In some embodiments the spacing between PLOs ranges from about 20 nm to about 200 µm, e.g., about 50 nm, 100 nm, 200 nm, 500 nm, 1 µm, 2 µm, 5 µm, 10 µm, 50 µm, 100 µm, 150 µm or another spacing distance from about 20 nm to 200 µm. In some embodiments the spacing between PLOs in the NPL array is regular. In other embodiments the spacing between PLOs in the NPL array varies. The skilled artisan will appreciate that in generating a NOPA according to the methods disclosed herein, it may be desirable or necessary to place some proteins in the assembly in closer proximity or more distal from each other in order to favor or prevent their interaction as necessary.

In some embodiments the PLOs provided in the NPL array include at least two to as many as 100 different PL sequences, e.g., 3, 4, 5, 6, 7, 10, 12, 15, 20, 30, 40, 60, 70, 80, 90 or another of different PL sequences in the NPL array. In some embodiments the PLOs in the NPL array comprise at least four different PL sequences. In other embodiments the PLOs in the NPL array comprise at least ten different PL sequences.

In some embodiments the NPL used in the method is a two dimensional array. In other embodiments the NPL array to be used is a three dimensional array.

Also disclosed herein are methods for in vitro biocatalysis, comprising the steps of: (i) providing a NOPA comprising first, second, and third nucleic acid anchor (NAA) enzymes, each NAA enzyme being linked to a solid support substrate surface by a nucleic acid duplex formed between an anchoring oligonucleotide and a protein localization oligonucleotide; (ii) contacting the NOPA with a reaction mix comprising a first substrate for the first NAA enzyme, whereby the first NAA enzyme converts the first substrate to a second substrate for the second NAA enzyme, the second NAA enzyme converts the second substrate to a third substrate for the third NAA enzyme, and the third NAA enzyme converts the third substrate to an end product, wherein: each NAA enzyme is covalently linked to an anchoring oligonucleotide comprising an anchoring sequence; the protein localization oligonucleotide comprises a protein localization sequence complementary to the anchoring sequence, and the protein localization oligonucleotide is covalently linked to the solid support substrate surface.

In some embodiments the NAA enzymes are fusion polypeptides comprising the amino acid sequence of a haloalkane dehalogenase or O6-alkylguanine-DNA alkyltransferase fused at the N-terminus or C-terminus of the fusion polypeptides. In some embodiments the NAA enzymes uses in the method are fusion polypeptides comprising the amino acid sequence of a haloalkane dehalogenase, and wherein the NAA enzymes are linked to the anchoring oligonucleotides via a covalent bond between the haloalkane dehalogenase and a halotag ligand.

In some embodiments the first, second, and third NAA enzymes are localized within a distance of between 20 and 200 μm of each other, e.g., about 20 nm to about 200 μm, e.g., about 50 nm, 100 nm, 200 nm, 500 nm, 1 μm, 2 μm, 5 μm, 10 μm, 50 μm, 100 μm, 150 μm or another spacing distance from about 20 nm to 200 μm. In some embodiments, the NAA enzymes are localized within a distance between 20 and 1,000 nm. In other embodiments the NAA enzymes are localized within a distance of 20 to 200 μm.

In some embodiments the NAA enzymes utilized in the biocatalysis method include the amino acids sequences of polyketide synthases, fungal cellulases, kinases, nitrogenases, proteases, phosphatases, oxidases, reductases, polymerases, hydrolases, lyases, transferases, isomerases, ligases, carboxylic acid reductases, oxidoreductases, glucosidases, glycoside hydrolases, glycases, dehydrogenases, enolases, synthases, endonucleases, exonucleases, lipases, oxygenases, cellulases, cyclases, esterases, or a combination thereof. For example, the method can be used to generate polyketides useful for drug screening or assembly of biochemical pathways useful for generation of biofuels, e.g., generation of ethanol from cellulosic materials. Other applications of the in vitro biocatalysis methods described herein include rational design of multiprotein pathways and substrate channeling, and novel enzyme-catalyzed reaction pathways having higher efficiency than naturally occurring enzymes.

In some embodiments at least one of the NAA enzymes is a polyketide synthase. In other embodiments at least one of the NAA enzymes to be used is a cellulase.

In some embodiments a first set of NAA-enzymes bound to a NPL array can be replaced by releasing the hybridized NAA enzymes by denaturation of the anchor oligonucleotide-protein localization oligonucleotide duplexes (e.g., by heat denaturation). Denaturation of the duplexes results in release of the bound NAA enzymes into solution, and can then be washed away from the NPL array, which can now be hybridized with another set of NAA enzymes. This process allows renewal of enzymes, which may lose activity over time, or introduction of new enzyme sets to drive complex, multistep biosynthetic reactions over multiple biosynthetic cycles.

The invention will be more fully understood upon consideration of the following non-limiting Examples.

EXAMPLES

The following examples are, of course, offered for illustrative purposes only, and are not intended to limit the scope of the present invention in any way. Indeed, various modifications of the invention in addition to those shown and described herein will become apparent to those skilled in the art from the foregoing description and the following examples and fall within the scope of the appended claims.

Example 1 Generation of NAA Proteins (AKA as "Bar Coded" Proteins)

Figure 6:
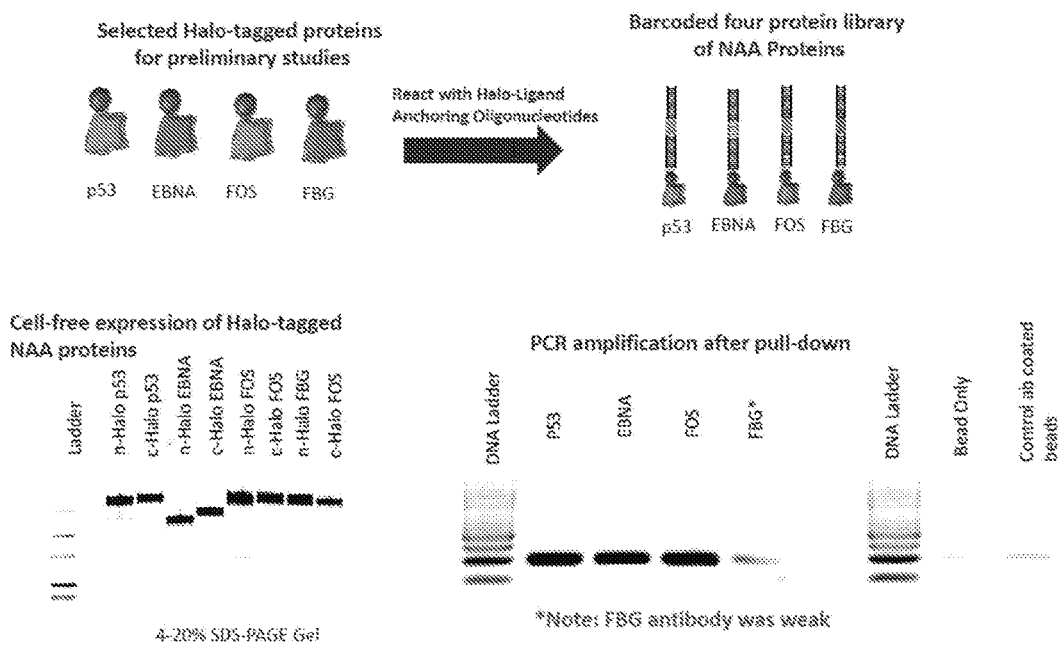
FIG. 6. Production of NAA (Halo-tagged) proteins. In the illustrated embodiment p53, EBNA, FOS, and FBG HaloTag® fusion proteins are reacted with an oligonucleotide-linked HaloLigand. The in vitro translated Halo-tagged fusion proteins are analyzed by SDS-PAGE as shown (bottom left). After immunoprecipitation with specific antibodies for each of the fusion proteins, PCR was carried out to amplify the linked anchor oligonucleotide for each NAA protein, and analyzed by gel electrophoresis. The correctly sized PCR product was detected for each immunoprecipitated protein, but not in the negative controls (e.g., beads only), demonstrating successful generation of halo-tagged fusion proteins covalently linked to anchoring (Halo-ligand) oligonucleotides.

Generation of Halotagged Fusion Proteins.

n-Halo and c-Halo tagged p53, EBNA, FOS and FBG were expressed in human coupled in vitro protein expression system (Thermo scientific). Protein expression was analyzed by incubating the proteins with 4 μM of Halo tag fluorescent ligand (Promega) followed by 4-20% SDS-PAGE gel analysis (FIG. 6, bottom left panel). Full length expression was observed for all proteins except for n-Halo tagged EBNA.

Generation of a DNA Bar Coded Four Protein Library.

Four unique Halo ligand-DNA anchor oligonucleotides (10 ng/μL) were added to c-Halo tagged p53, EBNA, FOS and FBG proteins. The samples were incubated on ice for 1 hour for covalent bond formation. Then, Halo ligand (4 mM) without a an anchoring oligonucleotide was added and incubated for 1 hour on ice to block any unbound sites. Equal concentration of NAA p53, EBNA, FOS and FBG were mixed together to make the four NAA protein library. The protein mixture was kept on ice.

Pull-Down Assays.

Magnetic Dynabeads protein G (Life technologies) particles were washed with ice cold PBST (PBS with 0.2% Tween-20) three times and incubated with 1:1000 diluted (PBST) anti-p53, anti-EBNA, anti-FOS and anti-FBG antibodies in separate wells at RT for 2 hours. Then, the beads were washed with ice-cold PBST five times and incubated with the four protein library at room temperature for two hours with shaking. The supernatant was removed and washed with ice-cold PBST six times and 100 μL of PBS was added to the beads after the final wash. The beads were stored at −20° C.

PCR Analysis.

The beads from the pull down assays were subjected to PCR with universal forward and reverse primers. The following thermal cycles were used for PCR: 98° C., 30 sec, 98° C., 10 sec; 58° C., 30 sec and 72° C., 1 sec; 20 cycles. After PCR, the supernatant was separated from the magnetic beads and the bands were resolved on a 1% agarose gel.

The PCR amplification of p53, EBNA, and FOS pull-down assays show amplified PCR products with ~100 bp, in agreement with expected size (FIG. 6, bottom right panel).

The results shown in FIG. 6 demonstrated the successful generation of four distinct NAA proteins labeled with four distinct anchoring oligonucleotides.

Example 2 Generation of a Nucleic Acid-Anchored Ordered Protein Assembly (NOPA) (Prophetic Example)

Generation of a Nucleic Acid-Guided Protein Localization (NPL) Array.

Amino or thiol modified single stranded PLOs are attached to a solid surface (silicon chips/glass slides etc) treated with epoxy silane or a mercaptosilanized glass support. The length of the spacer between the solid support and the PLO sequence could vary between 9 to 20 nucleotides. The optimum surface density of the PLO coverage is determined by varying the PLO concentration between 2 mM-20 mM.

Generation of NAA Proteins.

N-Halo or c-Halo tagged proteins are expressed in human coupled in vitro protein expression system (Thermo scientific). Unique Halo ligand-DNA AOs are added to each Halo tagged protein to generate the NAA proteins. Afterwards, any unbound sites are blocked by incubating the NAA proteins with a halo ligand without an AO. Equal concentration of NAA proteins are mixed together to make the NAA library.

DNA Directed Hybridization.

The NPL array is blocked with a blocking solution to reduce any non-specific binding and the NAA protein library is allowed to hybridize with the NPL array in a hybridization chamber at room temperature or at 37° C. in a buffer containing $Na_2HPO_4/NaH_2PO_4$ 0.1 M, NaCl 0.5 M, Tween 20 (0.65%), and PEG 4000 (2%). The optimum time for hybridization is determined by varying the time between 1 to 6 hours.

The invention has been described in connection with what are presently considered to be the most practical and preferred embodiments. However, the present invention has been presented by way of illustration and is not intended to be limited to the disclosed embodiments. Accordingly, those skilled in the art will realize that the invention is intended to encompass all modifications and alternative arrangements within the spirit and scope of the invention as set forth in the appended claims.

What is claimed is:

1. A method for generating a nucleic acid-anchored ordered protein assembly (NOPA), the method comprising the steps of:
   (i) providing a nucleic acid-guided protein localization (NPL) array comprising a plurality of single stranded protein localization oligonucleotides (PLOs) linked at a plurality of positions to a solid support substrate surface, wherein the plurality of PLOs comprise at least a first position-linked PLO comprising a first protein localization (PL) sequence and a second position-linked PLO comprising a second PL sequence;
   (ii) contacting the nucleic acid array with at least a first nucleic acid anchor (NAA) protein and a second NAA protein, wherein the first NAA is linked to an anchoring oligonucleotide comprising an anchoring sequence complementary to the first PL sequence, and the second NAA protein is linked to an anchoring oligonucleotide (AO) comprising an anchoring sequence complementary to the second PL sequence; and
   (iii) hybridizing, under protein compatible conditions, the AOs of the first and second NAA proteins with the first and second PLOs, whereby the at least first and second NAA proteins are localized to the first and second locations to form an ordered protein assembly.

2. The method of claim 1, wherein the NAA proteins are fusion polypeptides comprising the amino acid sequence of a haloalkane dehalogenase or O6-alkylguanine-DNA alkyltransferase fused at the N-terminus or C-terminus of the fusion polypeptides.

3. The method of claim 1, wherein: each NAA protein is a fusion polypeptide comprising the amino acid sequence of a haloalkane dehalogenase, each anchoring oligonucleotide comprises a 5' or 3' halotag ligand, and the haloalkane dehalogenase is covalently linked to the halotag ligand.

4. The method of claim 1, wherein the first and second PLOs are located between 20 nm and 200 µm of each other.

5. A nucleic acid-linked ordered protein assembly (NOPA), comprising
   (i) at least first and second single stranded protein localization oligonucleotides (PLOs) linked to a solid support substrate surface at separate positions, wherein each PLO comprises a protein localization (PL) sequence; and
   (ii) a first nucleic acid anchor (NAA) protein and a second NAA protein, wherein the first NAA is linked to an anchoring oligonucleotide (AO) comprising an anchoring sequence complementary to the first PL sequence, and the second NAA protein is linked to an anchoring oligonucleotide (AO) comprising an anchoring sequence complementary to the second PL sequence; wherein the first and second NAA proteins are bound to the first and second PL sequences by nucleic acid duplexes between the PL sequences and the anchoring sequences.

6. The NOPA of claim 5, wherein the NAA proteins are fusion polypeptides comprising the amino acid sequence of a haloalkane dehalogenase or O6-alkylguanine-DNA alkyltransferase fused at the N-terminus or C-terminus of the fusion polypeptides.

7. The NOPA of claim 6, wherein each NAA protein is a fusion polypeptide comprising the amino acid sequence of a haloalkane dehalogenase, each anchoring oligonucleotide comprises a 5' or 3' halotag ligand, and the haloalkane dehalogenase is covalently linked to the halotag ligand.

8. The NOPA of claim 5, wherein the separate positions are located between 20 nm and 200 µm of each other.

9. The NOPA of claim 5, wherein the NOPA comprises NAA proteins comprising at least ten different amino acid sequences.

* * * * *

UNITED STATES PATENT AND TRADEMARK OFFICE
CERTIFICATE OF CORRECTION

PATENT NO. : 10,351,842 B2
APPLICATION NO. : 15/310868
DATED : July 16, 2019
INVENTOR(S) : Joshua LaBaer It is certified that error appears in the above-identified patent and that said Letters Patent is hereby corrected as shown below:

In the Specification

Column 5, Line 63, "$Na_2HPO/NaH_2PO_4$" should be -- $Na_2HPO_4/NaH_2PO_4$ --.

Signed and Sealed this
Third Day of September, 2019

Andrei Iancu
*Director of the United States Patent and Trademark Office*

SEQUENCE LISTING

```
<160> NUMBER OF SEQ ID NOS: 1

<210> SEQ ID NO 1
<211> LENGTH: 297
<212> TYPE: PRT
<213> ORGANISM: Artificial Sequence
<220> FEATURE:
<223> OTHER INFORMATION: HaloTag linked derived from bacterial
      haloalkane dehalogenase

<400> SEQUENCE: 1

Met Ala Glu Ile Gly Thr Gly Phe Pro Phe Asp Pro His Tyr Val Glu
1               5                   10                  15

Val Leu Gly Glu Arg Met His Tyr Val Asp Val Gly Pro Arg Asp Gly
            20                  25                  30

Thr Pro Val Leu Phe Leu His Gly Asn Pro Thr Ser Ser Tyr Val Trp
        35                  40                  45

Arg Asn Ile Ile Pro His Val Ala Pro Thr His Arg Cys Ile Ala Pro
    50                  55                  60

Asp Leu Ile Gly Met Gly Lys Ser Asp Lys Pro Asp Leu Gly Tyr Phe
65                  70                  75                  80

Phe Asp Asp His Val Arg Phe Met Asp Ala Phe Ile Glu Ala Leu Gly
                85                  90                  95

Leu Glu Glu Val Val Leu Val Ile His Asp Trp Gly Ser Ala Leu Gly
            100                 105                 110

Phe His Trp Ala Lys Arg Asn Pro Glu Arg Val Lys Gly Ile Ala Phe
        115                 120                 125

Met Glu Phe Ile Arg Pro Ile Pro Thr Trp Asp Glu Trp Pro Glu Phe
    130                 135                 140

Ala Arg Glu Thr Phe Gln Ala Phe Arg Thr Thr Asp Val Gly Arg Lys
145                 150                 155                 160

Leu Ile Ile Asp Gln Asn Val Phe Ile Glu Gly Thr Leu Pro Met Gly
                165                 170                 175

Val Val Arg Pro Leu Thr Glu Val Glu Met Asp His Tyr Arg Glu Pro
            180                 185                 190

Phe Leu Asn Pro Val Asp Arg Glu Pro Leu Trp Arg Phe Pro Asn Glu
        195                 200                 205

Leu Pro Ile Ala Gly Glu Pro Ala Asn Ile Val Ala Leu Val Glu Glu
    210                 215                 220

Tyr Met Asp Trp Leu His Gln Ser Pro Val Pro Lys Leu Leu Phe Trp
225                 230                 235                 240

Gly Thr Pro Gly Val Leu Ile Pro Pro Ala Glu Ala Ala Arg Leu Ala
                245                 250                 255
```

-continued

```
Lys Ser Leu Pro Asn Cys Lys Ala Val Asp Ile Gly Pro Gly Leu Asn
            260                 265                 270

Leu Leu Gln Glu Asp Asn Pro Asp Leu Ile Gly Ser Glu Ile Ala Arg
        275                 280                 285

Trp Leu Ser Thr Leu Glu Ile Ser Gly
    290                 295
```